US006765636B2

(12) United States Patent
Iijima

(10) Patent No.: US 6,765,636 B2
(45) Date of Patent: Jul. 20, 2004

(54) LIQUID CRYSTAL DISPLAY DEVICE AND ELECTRONIC APPARATUS

(75) Inventor: Chiyoaki Iijima, Jma (JP)

(73) Assignee: Seiko Epson Corporation, Tokyo (JP)

(*) Notice: Subject to any disclaimer, the term of this patent is extended or adjusted under 35 U.S.C. 154(b) by 0 days.

(21) Appl. No.: 10/614,981

(22) Filed: Jul. 9, 2003

(65) Prior Publication Data

US 2004/0075792 A1 Apr. 22, 2004

(30) Foreign Application Priority Data

Jul. 23, 2002  (JP) ........................................ 2002-214297

(51) Int. Cl.[7] .............................................. G02F 1/1335
(52) U.S. Cl. ........................................ 349/96; 349/113
(58) Field of Search .......................... 349/96, 98, 103, 349/113, 114; 359/486, 487, 490, 491, 494, 495, 500

(56) References Cited

U.S. PATENT DOCUMENTS

2002/0085146 A1 * 7/2002 Miyazaki .................... 349/96
2003/0218701 A1 * 11/2003 Kawakami .................. 349/65

FOREIGN PATENT DOCUMENTS

| JP | A 2001-91747   | 4/2001 |
| JP | A 2001-166138  | 6/2001 |
| JP | A 2001-512248  | 8/2001 |
| JP | A 2002-277636  | 9/2002 |

* cited by examiner

Primary Examiner—Toan Ton
Assistant Examiner—Tai Duong
(74) Attorney, Agent, or Firm—Oliff & Berridge, PLC

(57) ABSTRACT

The invention provides a transflective liquid crystal display device which can be operated in a reflective mode and a transmissive mode, which performs high-contrast display especially in the transmissive mode. A liquid crystal display device is constructed such that the transmissive polarization axis of a lower polarizing layer is substantially orthogonal to that of a lower reflective polarizing layer, and the degree of polarization of the lower polarizing layer is greater than that of the lower reflective polarizing layer. With this structure, the liquid crystal display device has enhanced display brightness and achieves high-contrast display in the transmissive mode.

5 Claims, 5 Drawing Sheets

LIQUID CRYSTAL DISPLAY DEVICE AND ELECTRONIC APPARATUS

BACKGROUND OF THE INVENTION

1. Field of Invention

The present invention relates to liquid crystal display devices and electronic apparatuses. More specifically, the invention relates to a transflective liquid crystal display device which performs high-contrast display in a transmissive mode.

2. Description of Related Art

Since reflective liquid crystal display devices are not equipped with a light source, such as a backlight, and thus consume less power, they are used in the related art for a variety of portable electronic apparatuses, display units of other apparatuses serving as ancillary equipment, and so forth.

However, since they perform display by utilizing external light, such as natural light or illumination light, they surfer from the problem of poor visibility of the display in dark places. To address or solve this problem, another related art liquid crystal display device uses external light in bright places in the same fashion as the usual reflective liquid crystal display device, and uses an internal light source in dark places so as to achieve highly visible display. That is, this liquid crystal display device combines reflective display type and transmissive display type, and by switching the display type between a reflective mode and a transmissive mode in accordance with the brightness of the ambient light, produces clear display even in a dark environment while reducing power consumption. In this specification, the liquid crystal display device of this type is referred to as "a transflective liquid crystal display device".

In another related art transflective liquid crystal display device, a reflective film which is made from a metal film composed of aluminum or the like, and which has slits for light transmission, is formed on the inner surface of a lower substrate. In this case, light emitted from a backlight disposed on the outer surface of the lower substrate passes through the slits so as to contribute to transmissive display, while light coming from an upper substrate is reflected from the reflective film so as to contribute to reflective display, whereby the reflective film serves as a transflective film.

SUMMARY OF THE INVENTION

Although the liquid crystal display device described above can perform highly visible display regardless of the presence of external light, there is a problem in that the display brightness is insufficient in the transmissive mode compared to the reflective mode. A significant reason for this problem is the fact that the amount of light contributing to display in the transmissive mode comes only from the amount of light passing through the slits formed in the reflective film.

Also, in transflective liquid crystal display devices having other structures, it is difficult to achieve well-balanced display between the reflective mode and the transmissive mode. For example, when conditions for achieving bright, less color-fringing display in the reflective mode are set, the contrast of the display in the transmissive mode is sometimes unsatisfactory; whereas, when other conditions to achieve high-contrast display in the transmissive mode are set, the display in the reflective mode sometimes exhibits color fringing.

The present invention addresses or solves the above and/or other problems, and provides a transflective liquid crystal display device which can be operated in a reflective mode and a transmissive mode, which performs bright display both in the reflective and transmissive modes, and which also performs high-contrast display especially in the transmissive mode. The present invention also provides an electronic apparatus equipped with this liquid crystal display device.

In order to address or achieve the above, a liquid crystal display device according to the present invention, having a structure in which a liquid crystal layer is sandwiched between mutually opposing upper and lower substrates-and display is performed by switching the display mode between a transmissive mode and a reflective mode, includes an upper polarizing layer disposed above the liquid crystal layer; a lower reflective polarizing layer disposed below the liquid crystal layer; a lower polarizing layer disposed below the lower reflective polarizing layer; and an illumination device disposed on the outer surface side of the lower substrate. The lower reflective polarizing layer includes light-transmissive portions formed therein, the transmissive polarization axis of the lower polarizing layer is substantially orthogonal to that of the lower reflective polarizing layer, and the degree of polarization of the lower polarizing layer is greater than that of the lower reflective polarizing layer. When the transmittances of linearly polarized light traveling, in a polarizing layer, parallel and orthogonally to the transmissive polarization axis thereof are respectively defined by T1 and T2, the degree of polarization of the polarizing layer is given by $(T1-T2)/(T1+T2)\times 100(\%)$ in the present invention.

The liquid crystal display device having the above-mentioned structure enhances display brightness and performs high-contrast display in the transmissive mode, in addition to maintaining display brightness in the reflective mode, whereby bright display can be achieved in both the reflective and transmissive modes. In other words, since the lower reflective polarizing layer having the light-transmissive portions formed therein can be used as a transflective film in the present invention, light emitted from the illumination device is transmitted through the light-transmissive portions so as to contribute to transmissive display. Since the light transmitted through the lower polarizing layer and then reflected from the lower reflective polarizing layer can be recycled, the brightness of the display in the transmissive mode is enhanced. In addition, the liquid crystal display device is constructed such that the transmissive polarization axis of the lower polarizing layer is substantially orthogonal to that of the lower reflective polarizing layer, and the degree of polarization of the lower polarizing layer is greater than that of the lower reflective polarizing layer. Accordingly, for example, light traveling orthogonally to the transmissive polarization axis of the lower polarizing layer (i.e., light traveling parallel to the transmissive polarization axis of the lower reflective polarizing layer) is unlikely transmitted through the lower polarizing layer, and even when the light traveling orthogonally to the transmissive polarization axis of the lower polarizing layer is transmitted therethrough, since the lower reflective polarizing layer has a relatively small degree of polarization, light transmitted through the lower polarizing layer is unlikely transmitted through the lower reflective polarizing layer, thereby reducing or preventing light from escaping. As a result, a liquid crystal display device having enhanced display contrast in the transmissive mode and exhibiting excellent display characteristics can be provided.

In the liquid crystal display device, when the degrees of polarization of the lower polarizing layer and the lower reflective polarizing layer are respectively reduced or defined by Pa and Pr, the condition $Pa \geq 1.1 \times Pr$ is preferably satisfied. In this case, the light-escaping mentioned above can be more effectively reduced or prevented.

The foregoing lower reflective polarizing layer may be formed by a laminate of dielectric interference films having a prismatic shape. More particularly, the lower reflective polarizing layer may be a so-called three-dimensional photonic crystal layer formed by a substrate having a plurality of grooves periodically formed on the upper surface thereof and by pluralities of two types of layers which are respectively composed of Si (silicon) and $SiO_2$ (silicon dioxide) and which are deposited alternately on the substrate. In this case, components of incident light traveling perpendicularly and parallel to the grooves of the substrate are respectively transmitted through and reflected from the photonic crystal. That is, whether the incident light is transmitted through the dielectric interference films or not depends on the directional relationship between the incident light and the foregoing prism shape.

Also, the foregoing lower reflective polarizing layer may be made from a metal reflective film having a plurality of fine, slit-like apertures formed therein. More particularly, the lower reflective polarizing layer may be formed by a substrate and a highly reflective metal film composed of aluminum or the like, which is formed on the substrate and which has a plurality of slits formed therein at a predetermined pitch. In this case, components of incident light traveling parallel and orthogonally to the longitudinal direction of the slits are respectively reflected from and transmitted through the lower reflective polarizing layer.

An electronic apparatus according to the present invention includes the above-mentioned liquid crystal display device according to the present invention. With this structure, an electronic apparatus equipped with an excellent display unit which performs high-contrast display in the transmissive mode can be achieved.

DETAILED DESCRIPTION OF PREFERRED EMBODIMENTS

Exemplary embodiments of the present invention are described below with reference to the accompanying drawings.
(Exemplary Liquid Crystal Display Device)

Figure 1:
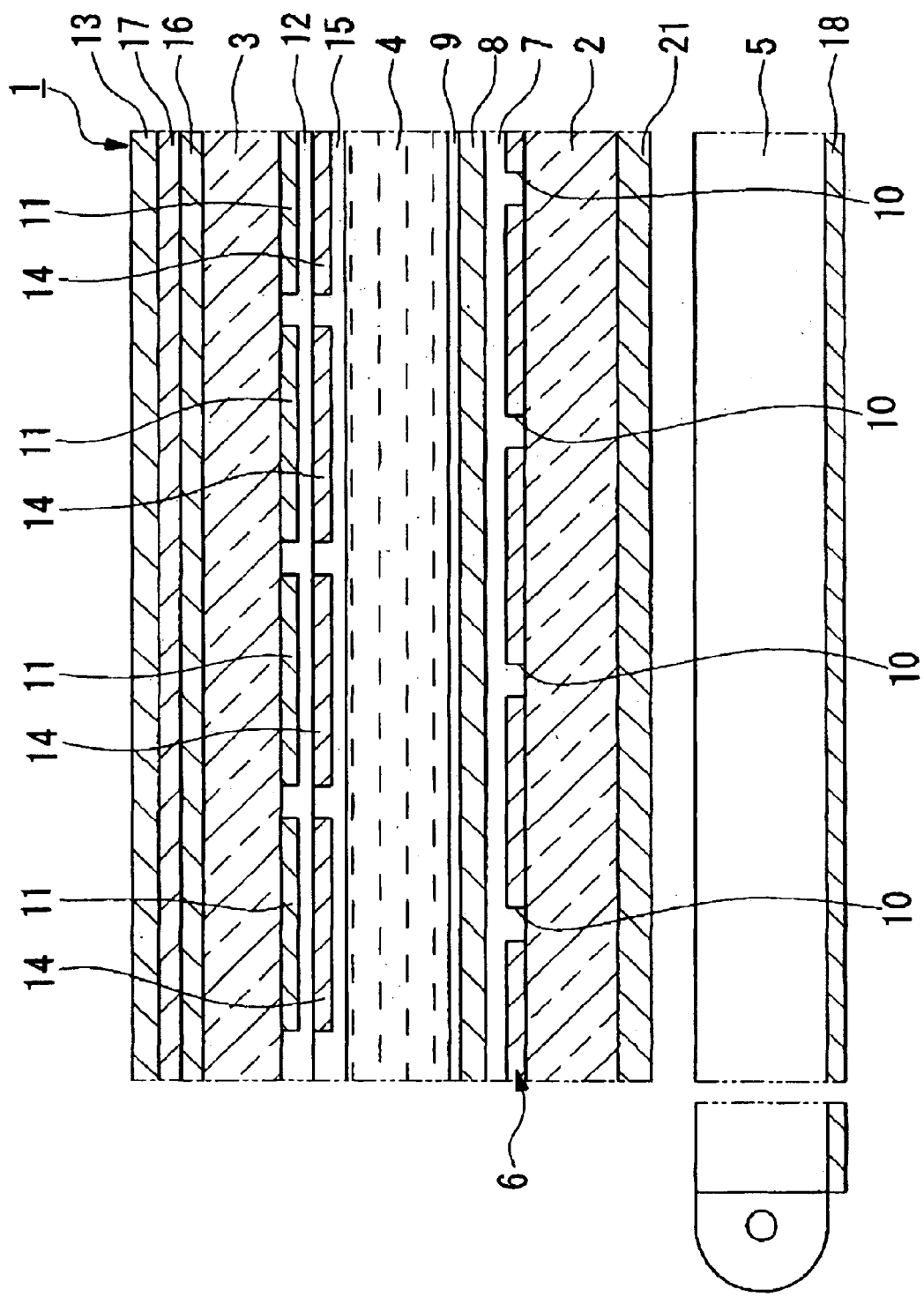
FIG. 1 is a partial sectional view of a liquid crystal display device according to an exemplary embodiment of the present invention.

FIG. 1 is a partial sectional view of the structure of a liquid crystal display device according to a first exemplary embodiment. The liquid crystal display device according to this exemplary embodiment is an example of a passive-matrix, transflective color liquid crystal display device. The thickness and the ratios of the dimensions of each component illustrated in the following figures have been appropriately modified such that the component can be easily viewed in each figure.

As shown in FIG. 1, a liquid crystal display device 1 according to this exemplary embodiment is schematically constructed by a liquid-crystal display panel, having a structure in which a lower substrate 2 and an upper substrate 3 are disposed so as to oppose each other and a liquid crystal layer 4 composed of STN (super twisted nematic) liquid crystal is sandwiched between the lower and upper substrates 2 and 3, and by a backlight (illumination device) 5 disposed at the rear side of the liquid crystal panel (on the outer surface side of the lower substrate 2). In this specification, the side of each of the substrates 2 and 3 close to the liquid crystal layer 4 is called the inner surface side, and its opposite side is called the outer surface side.

The lower substrate 2 composed of glass, resin, or the like has a lower reflective polarizing layer 6 and an insulating film 7 deposited in that order on the inner surface side thereof, the insulating film 7 has scanning electrodes 8 formed thereon, extending horizontally in the figure in a striped pattern and made from a transparent conductive film composed of ITO (indium tin oxide) or the like; and an alignment film 9 composed of polyimide or the like is deposited so as to cover the scanning electrodes 8. Also, the lower reflective polarizing layer 6 has a slit (an aperture) 10 at each pixel so that light emitted from the backlight 5 is transmitted therethrough. In addition, the lower substrate 2 has a lower polarizer (a lower polarizing layer) 21 disposed on the outer surface side thereof The lower polarizer 21 is formed such that its transmissive polarization axis is substantially orthogonal to that of the lower reflective polarizing layer 6, and such that the degree of its polarization is greater than that of the lower reflective polarizing layer 6. More particularly, when the degrees of polarization of the lower polarizer 21 and the lower reflective polarizing layer 6 are respectively defined by Pa and Pr, the condition $Pa \geq 1.1 \times Pr$ is satisfied. For example, in this exemplary embodiment, Pa and Pr are arranged so as to be equal to 99% and 90%, respectively.

On the inner surface side of the upper substrate 3, composed of glass, resin, or the like, color filters 11 for red, green, and blue, extending in a direction perpendicular to the plane of the figure, are periodically arranged in that color order so as to be orthogonal to the scanning electrodes 8 of the lower substrate 2, and the color filters 11 have a planarizing film 12 deposited thereon so as to planarize irregularities caused by the color filters 11. The planarizing film 12 has signal electrodes 14 formed thereon in a striped pattern, made from a transparent conductive film composed of ITO (indium tin oxide) or the like and extending in a direction perpendicular to the plane of the figure, and the signal electrodes 14 have an alignment film 15 deposited thereon, composed of polyimide or the like. Also, the upper substrate 3 has a front diffuser 16, a retardation film 17, and an upper polarizer (an upper polarizing layer) 13 deposited in that order on the outer surface side thereof. In addition, the backlight 5 has a reflector 18 disposed on the bottom side thereof (on the opposite side of the liquid crystal panel).

Figure 3:
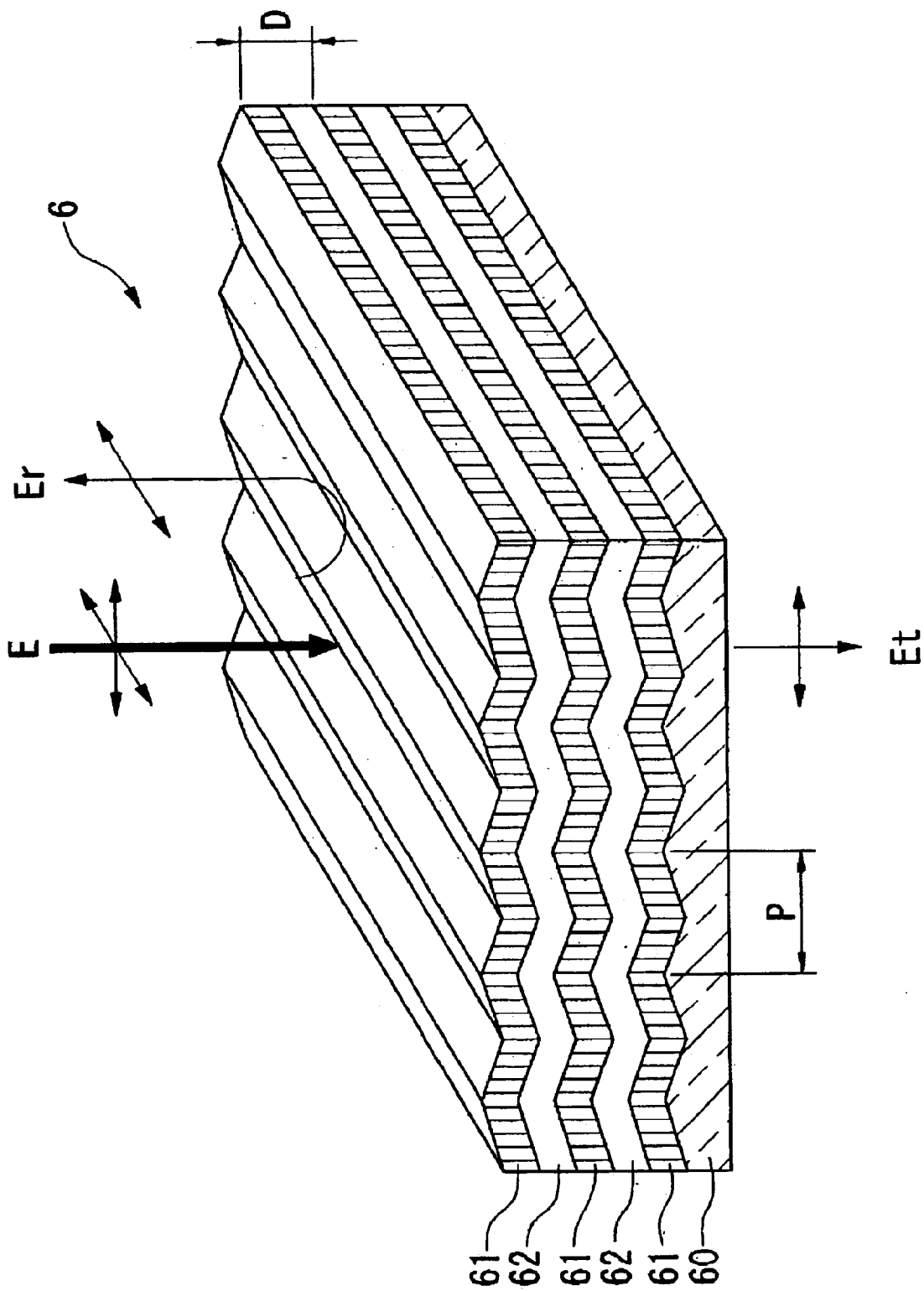
FIG. 3 is a perspective view of an exemplary lower reflective polarizing layer of the liquid crystal display device according to the present invention.

As shown in FIG. 3, the lower reflective polarizing layer 6 includes a laminate of dielectric interference films having a prismatic shape. The lower reflective polarizing layer 6 shown in FIG. 3 is a so-called three-dimensional photonic crystal layer formed by a substrate 60 having a plurality of grooves periodically formed on the upper surface thereof and by pluralities of layers 61 and 62 which are mainly composed of Si (silicon) and $SiO_2$ (silicon dioxide), respectively, and which are deposited alternately on the substrate 60. Since the photonic crystal layer having a structure in which the pluralities of layers having a prismatic shape are deposited as described above has anisotropic light-propagation characteristics, when light is incident on the photonic crystal layer from above in the figure, components of the incident light traveling perpendicularly and parallel to the grooves of the substrate 60 are respectively transmitted through and reflected from the photonic crystal layer.

More particularly, light Et transmitted through the lower reflective polarizing layer 6 shown in FIG. 3 becomes polarized light traveling perpendicularly to the grooves of the substrate 60, and light Er reflected therefrom becomes polarized light traveling parallel to the grooves. The deposition pitch D between a pair of the layers 62 and 62 is about 0.1 $\mu$m, and the pitch P between each groove formed on the substrate 60 is about 3 to 5 $\mu$m. In this exemplary embodiment, the transmissive polarization axis of the lower reflective polarizing layer 6 is arranged so as to extend perpendicularly to the plane of FIG. 1. That is, the grooves of the substrate 60 shown in FIG. 3 are formed so as to extend parallel to the plane of FIG. 1, and the apertures 10 are disposed in corresponding parts of the lower reflective polarizing layer 6 so that light emitted from the backlight 5 is transmitted through the apertures 10.

Figure 4:
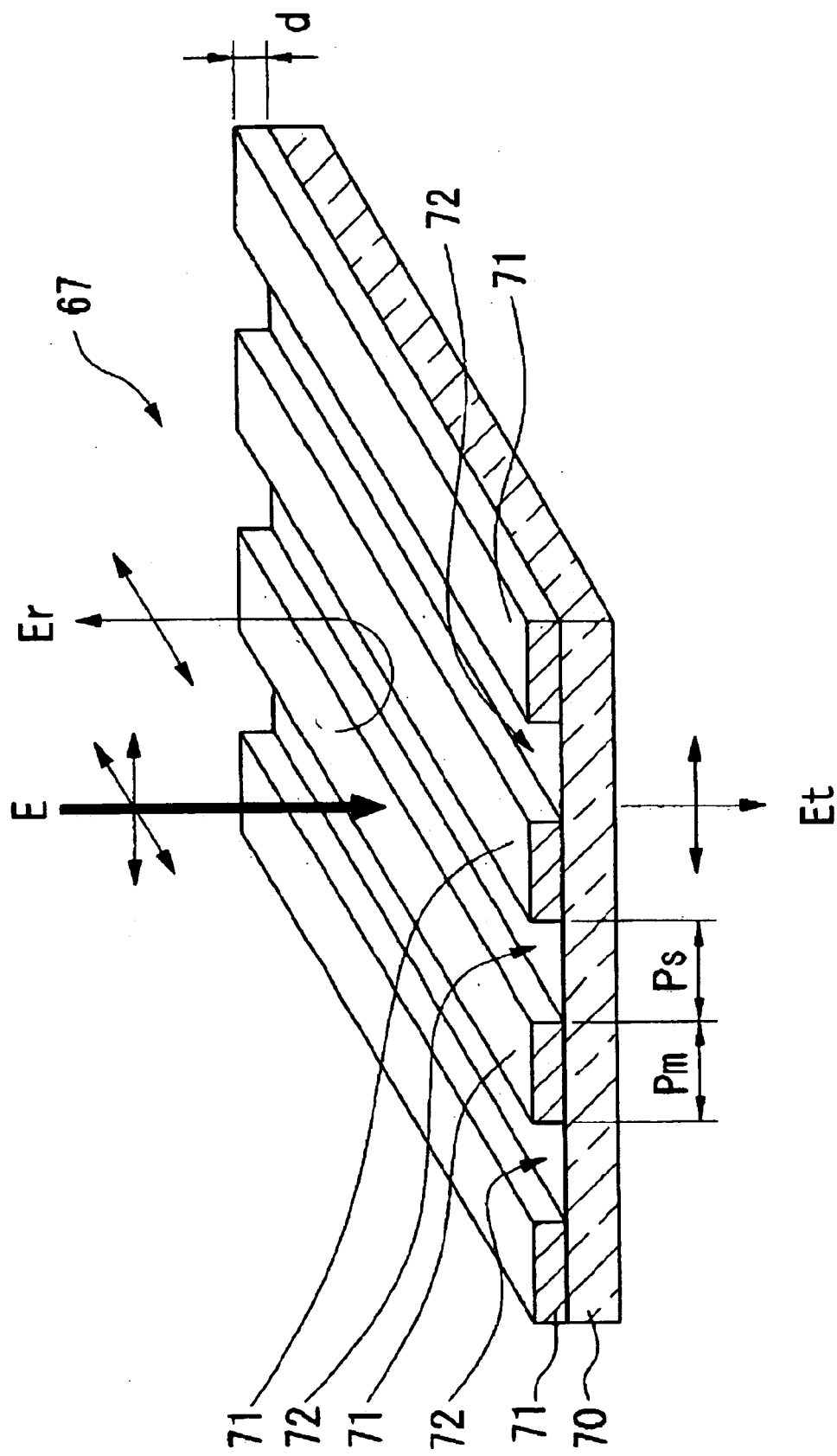
FIG. 4 is a perspective view of another exemplary lower reflective polarizing layer of the liquid crystal display device according to the present invention.

As an exemplary modification of the lower reflective polarizing layer 6, a lower reflective polarizing layer 67 made from a metal reflective film having a plurality of fine, slit-like apertures formed therein, as shown in FIG. 4, may be used. FIG. 4 is a perspective view illustrating an example reflective polarizing layer made from a metal reflective film having a plurality of fine slits formed therein. The lower reflective polarizing layer 67 in this case has a structure in which a metal reflective film 71 composed of aluminum, silver, or the like is formed on a substrate 70 and has a plurality of slits 72 formed therein at a predetermined pitch. The plurality of slits 72 extend parallel to each other, and all of the slits 72 have substantially the same width Ps. Although the dimensions of the metal reflective film 71 are not limited to particular values, each strip of the metal reflective film 71 in this case has a thickness "d" in the range from about 100 nm to 400 nm and a width Pm in the range from 30 nm to 300 nm, and each metal reflective film 71 has a width Pm in the range from 30 nm to 300 nm.

When light is incident on the reflective polarizing layer 67 having the above-mentioned structure, from the upper surface side thereof, components of the light traveling parallel and orthogonally to the longitudinal direction of the slits 72 are respectively reflected therefrom and transmitted therethrough. In other words, the light Et transmitted through the reflective polarizing layer 67 shown in FIG. 4 becomes polarized light traveling perpendicularly to the slits 72, and the light Er reflected from the reflective polarizing layer 67 becomes polarized light traveling parallel to the slits 72. Also, in this exemplary embodiment, the transmissive polarization axis of the lower reflective polarizing layer 67 is arranged so as to extend perpendicularly to the plane of FIG. 1. That is, the longitudinal direction of the slits 72 shown in FIG. 4 is arranged so as to extend parallel to the plane of FIG. 1, and each aperture 10 is formed in a part of the reflective polarizing layer 67 such that light emitted from the backlight 5 is transmitted therethrough.

Figure 2B:
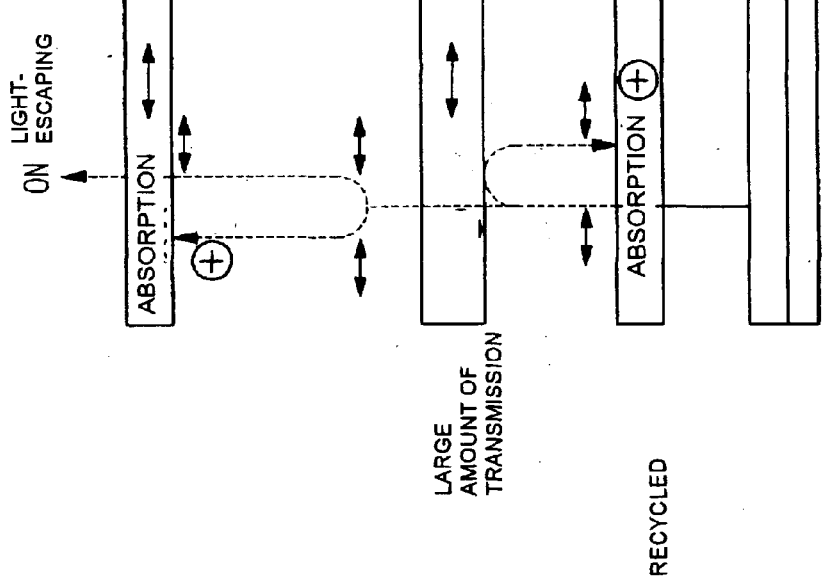
FIGS. 2A and 2B are schematics of the display characteristics of the liquid crystal display device shown in FIG. 1.
Figure 2A:
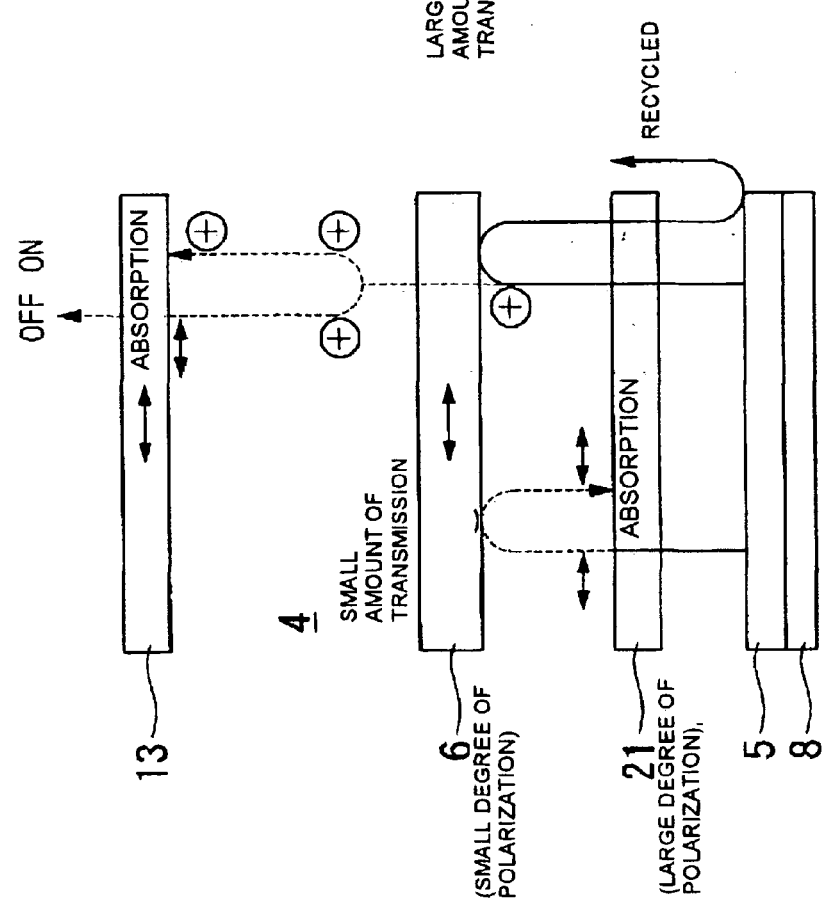

In the liquid crystal display device 1 according to this exemplary embodiment, as described above, the transmissive polarization axis of the lower polarizer 21 extends almost orthogonally to that of the lower reflective polarizing layer 6, and the degree of polarization (for example, Pa=99%) of the lower polarizer 21 is greater than the degree of polarization (for example, Pr=90%) of the lower reflective polarizing layer 6. Also, the lower reflective polarizing layer 6 has the slits 10 formed therein so as to serve as a transflective film. Referring now to FIG. 2, the display characteristics of the liquid crystal display device 1 according to this exemplary embodiment is described below. FIGS. 2A and 2B are schematics of significant parts of some components illustrating the display characteristics of the liquid crystal display device 1.

In this case, for example, light transmitted through the lower polarizer 21 and then reflected from the lower reflective polarizing layer 6 can be recycled, as shown at the right side in FIG. 2A. Also, since the degree of polarization of the lower polarizer 21 is relatively large, light traveling orthogonally to the transmissive polarization axis (in FIG. 2, in a direction perpendicular to the plane of the figure) of the lower polarizer 21 is unlikely transmitted through the lower polarizer 21. Even when the light traveling orthogonally to the transmissive polarization axis of the lower polarizer 21 is transmitted through the lower polarizer 21, as shown at the left side of FIG. 2A, since the degree of polarization of the lower reflective polarizing layer 6 is relatively small, light transmitted through the lower polarizer 21 is unlikely transmitted through the lower reflective polarizing layer 6.

On the other hand, as shown in FIG. 2B, when the degrees of polarization of a lower polarizer 21' and a lower reflective polarizing layer 6' are, for example, relatively small and large, respectively, light traveling orthogonally to the transmissive polarization axis of the lower polarizer 21' is easily transmitted therethrough. Also, the light transmitted through the lower polarizer 21' is also easily transmitted through the lower reflective polarizing layer 6', thereby leading to the problem of light-escaping and accordingly to a deteriorated contrast.

As described above, the liquid crystal display device 1 shown in FIG. 2A according to this exemplary embodiment is more likely to prevent light from escaping, especially in a transmissive mode, compared to that having the structure shown in FIG. 2B, thereby leading to an enhanced contrast in the transmissive mode.

(Exemplary Electronic Apparatus)

Exemplary electronic apparatuses, each equipped with the liquid crystal display device according to the foregoing exemplary embodiment, are described below.

Figure 5A:
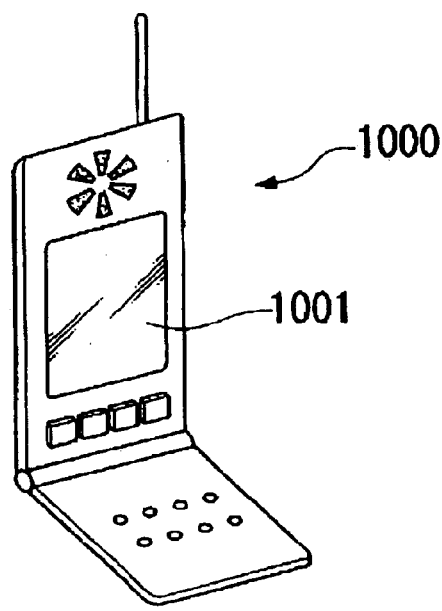
FIGS. 5A to 5C are perspective views illustrating exemplary electronic apparatuses according to the present invention.

FIG. 5A is a perspective view of an exemplary portable phone. In this figure, reference numerals 1000 and 1001, respectively, represent a main body of the portable phone and a liquid crystal display unit using the foregoing liquid crystal display device according to the foregoing exemplary embodiment.

Figure 5B:
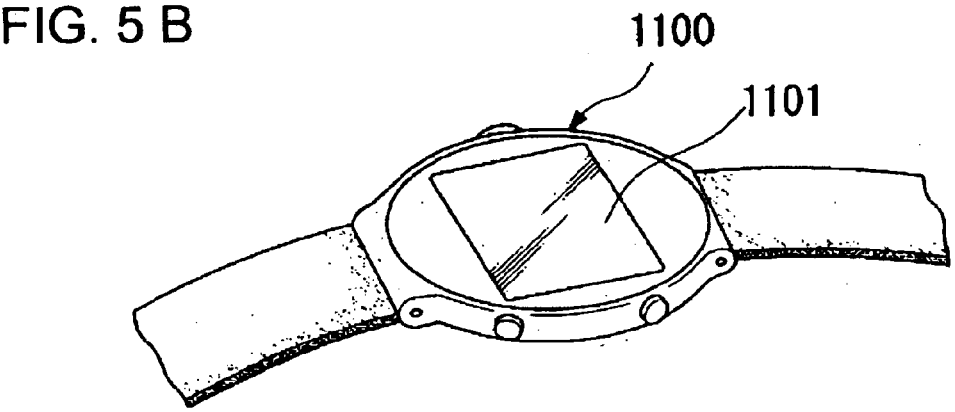

FIG. 5B is a perspective view of an exemplary wristwatch-type electronic apparatus. In this figure, reference numerals 1100 and 1101, respectively, represent a main body of the watch and a liquid crystal display unit using the foregoing liquid crystal display device according to the foregoing exemplary embodiment.

Figure 5C:
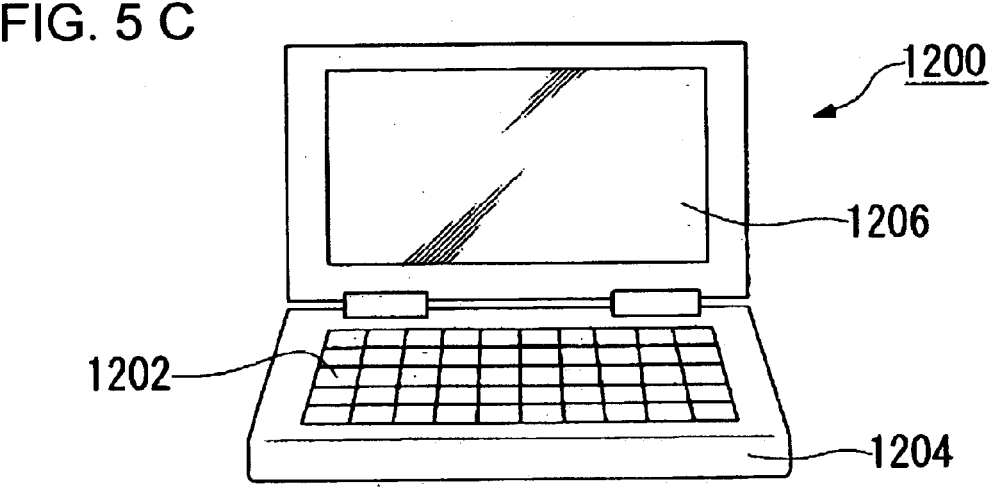

FIG. 5C is a perspective view of an example portable information processor, such as a word processor or a personal computer. In FIG. 5(C), the reference numerals 1200, 1202, 1204, and 1206, respectively, represent an information processor, an input unit including a keyboard, a main body of the information processor, and a liquid crystal display unit using the foregoing exemplary liquid crystal display device according to the foregoing exemplary embodiment.

Each of the electronic apparatuses shown in FIGS. 5A to 5C is equipped with the corresponding liquid crystal display unit using the liquid crystal display device according to the foregoing exemplary embodiment, thereby achieving an electronic apparatus which is equipped with a display unit featuring bright display in the transmissive mode.

EXAMPLES

By varying the degrees of polarization Pa and Pr of the lower polarizer 21 and the lower reflective polarizing layer 6, the contrasts of the liquid crystal display device 1 according to the foregoing exemplary embodiment in transmissive display mode were measured. The results are shown in Table 1, wherein the contrast is evaluated as "excellent", "good", and "acceptable", respectively, when it is 10 or more, 5 or more but less than 10, and less than 5.

TABLE 1

|  | Pa (%) | Pr (%) | Pa/Pr | Evaluation of Contrast |
| --- | --- | --- | --- | --- |
| Example 1 | 99 | 90 | 1.1 | Excellent |
| Example 2 | 95 | 80 | 1.18 | Excellent |
| Example 3 | 90 | 85 | 1.06 | Good |
| Comparative Example 1 | 85 | 90 | 0.94 | Acceptable |

In Examples 1 and 2 respectively having the ratios Pa/Pr of 1.1 and 1.18, the contrasts in transmissive display were respectively 14 and 15, resulting in high-contrast, highly visible display. Meanwhile, in Example 3 having the ratio Pa/Pr of 1.06, its contrast in transmissive display was 7, resulting in slightly inferior display compared to those of Examples 1 and 2. Also, in Comparative Example 1 having the ratio Pa/Pr of 0.94, its contrast in transmissive display was 4, which is smaller than those of Examples 1 to 3.

The above-mentioned results demonstrate that, when the ratio Pa/Pr of the degrees of polarization Pa and Pr of the lower polarizing layer 21 and the lower reflective polarizing layer 6, respectively, is at least 1.1, the liquid crystal display device 1 according to this exemplary embodiment achieves high-contrast display in the transmissive mode, and that, by setting Pa greater than Pr, the liquid crystal display device 1 achieves highly visible transmissive display.

Advantages

As described above, since the liquid crystal display device according to the present invention is constructed such that the transmissive polarization axis of the lower polarizing layer is substantially orthogonal to that of the lower reflective polarizing layer, and the degree of polarization of the lower polarizing layer is greater than that of the lower reflective polarizing layer, the liquid crystal display device has enhanced display brightness and achieves high-contrast display in the transmissive mode.

What is claimed is:

1. A transflective liquid crystal display device, comprising:

opposing upper and lower substrates;

a liquid crystal layer sandwiched between the opposing upper and lower substrates, display being performable by switching a display mode between a transmissive mode and a reflective mode;

an upper polarizing layer disposed above the liquid crystal layer;

a lower reflective polarizing layer disposed below the liquid crystal layer;

a lower polarizing layer disposed below the lower reflective polarizing layer; and an illumination device disposed on the outer surface side of the lower substrate, the lower reflective polarizing layer including light-transmissive portions formed therein, a transmissive polarization axis of the lower polarizing layer being substantially orthogonal to a transmissive polarization axis of the lower reflective polarizing layer, and a degree of polarization of the lower polarizing layer being greater than a degree of polarization of the lower reflective polarizing layer.

2. The liquid crystal display device according to claim 1, when the degrees of polarization of the lower polarizing layer and the lower reflective polarizing layer are respectively defined by Pa and Pr, the condition Pa≧1.1×Pr being satisfied.

3. The liquid crystal display device according to claim 1, the lower reflective polarizing layer including a laminate of dielectric interference films having a prismatic shape.

4. The liquid crystal display device according to claim 1, the lower reflective polarizing layer including a metal reflective film having a plurality of fine, slit-like apertures formed therein.

5. An electronic apparatus, comprising:

the liquid crystal display device according to claim 1.

* * * * *